(12) United States Patent
Kohn et al.

US006362008B1

(10) Patent No.: US 6,362,008 B1
(45) Date of Patent: Mar. 26, 2002

(54) GENERIC SIGNALLING MECHANISM FOR DETECTION OF ANALYTES

(76) Inventors: Barbara A. Kohn; Jack L. Radlo, both of c/o VICAM L.P., 313 Pleasant St., Watertown, MA (US) 02472

( * ) Notice: Subject to any disclaimer, the term of this patent is extended or adjusted under 35 U.S.C. 154(b) by 0 days.

(21) Appl. No.: 09/337,365

(22) Filed: Jun. 21, 1999

Related U.S. Application Data

(63) Continuation-in-part of application No. 09/161,454, filed on Sep. 28, 1998, now abandoned.
(60) Provisional application No. 60/068,567, filed on Dec. 23, 1997.

(51) Int. Cl.[7] ............................................... G01N 33/53
(52) U.S. Cl. ...................... 436/514; 435/7.1; 435/7.92; 435/7.93; 435/794; 435/7.95; 435/810; 435/975; 436/518; 436/528; 436/539
(58) Field of Search ................................ 435/7.1, 7.92, 435/7.93, 7.94, 7.95, 810, 975; 436/518, 528, 539, 514

(56) References Cited

U.S. PATENT DOCUMENTS

| | | | |
|---|---|---|---|
| 3,896,217 A | | 7/1975 | Johnson |
| 3,996,345 A | * | 12/1976 | Ullman et al. |
| 4,895,809 A | | 1/1990 | Schlabach et al. |
| 4,935,147 A | * | 6/1990 | Ullman et al. |
| 4,977,077 A | | 12/1990 | Ngo et al. |

FOREIGN PATENT DOCUMENTS

EP    0040365 A1    11/1981

OTHER PUBLICATIONS

J. Agric. Food Chem. 1987, 35, 182–86 "Transmission of (14C)Deoxynivalenol . . . " Prelusky, Dan B. et al.
J. Agric. Food Chem. 1988, 36, 663–68 "Enzyme–Linked Immunosorbent Assay . . . " Casale, William L. et al.
J. Agric. Food Chem. 1996, 44, 1041–46 "Fiber–Optic immunosensor for the . . . " Thompson, Vicki S. et al.
J. AOAC International 81 (2) 1998, 448–452 "One–Step Solid–Phase . . . " Malone, Bruce R. et al.

\* cited by examiner

*Primary Examiner*—Bao-thuy L. Nguyen
(74) *Attorney, Agent, or Firm*—Tom Hunter; Law Offices of Jonathan Alan Quine

(57) ABSTRACT

A generic signaling assay method comprising an affinity matrix for the detection of low molecular weight compositions is provided. A test sample is mixed with a predetermined amount of a substance conjugated to at least two molecules of the target analyte. When the test sample containing the multiple-analyte conjugated substance is passed over the immunoaffinity column, the antibodies can bind competitively to two species: free analyte and multiple-analyte conjugated substance. The column is then exposed to a second tagged antibody. Upon elution, high label activity is seen in a clean sample. Conversely, only a small amount of the label activity is detected in the eluant of a test sample that is highly contaminated with the free analyte.

20 Claims, No Drawings

GENERIC SIGNALLING MECHANISM FOR DETECTION OF ANALYTES

This application is a continuation in part of application 09/161,454 filed Sep. 28, 1998, now abandoned, which is a continuation of provisional application No. 60/068,567 filed on Dec. 23, 1997, which is hereby incorporated by reference. In the parent application, an invention is described which is directed to non-invasive screening procedures for assessing the exposure of humans and animals to environmentally occurring analytes. In particular, the parent application is directed to compositions and processes for the detection of small analyte molecules by utilizing a generic signaling mechanism which is applicable for detecting any small analyte. This application describes a second method for detection of any small analyte, particularly analytes that are hydrophobic or are difficult to chemically modify.

BACKGROUND OF THE INVENTION

The general class of small analytes which are to be assayed includes small molecular weight (about 10,000 daltons or less, preferably about 6,000 daltons or less, which is less than the size usable in a sandwich assay format, and which is capable of being recognized and bound by a ligand) pesticides, drugs, toxins, mycotoxins and drug metabolites, and further includes trichothecenes, fumonisins, antibiotics, and fragments of microorganisms, such as bacteria, parasites, viruses, yeast and mold, and fragments of mammalian cells. In particular, non-invasive screening procedures for assessing the exposure of humans to these substances require the ability to quantify both the target analyte and in some cases, metabolites, such as hydroxylated derivatives which include Aflatoxin $M_1$, derived by hydroxylation from Aflatoxin $B_1$, and/or other metabolites in body fluids such as milk, serum and urine.

Both the parent and the present inventions relate to a small analyte detecting assay which is novel because, in one test, it incorporates the best aspects of Enzyme Linked Immunosorbent Assay (ELISA) and Immunoaffinity chromatography (IA), but is not one or the other, since in contrast to ELISA, neither the parent nor the present invention use an enzyme signaling method, and in contrast to IA, the parent and present inventions depend on a competition and, therefore, do not result in isolation solely of purified target analyte, nor in isolation of target analyte at high efficiency. In addition, the inventions can be applied as general signal generation methods for a variety of target analytes.

Previously, with each new target analyte, a visualization approach specific to that target analyte was needed, which requires great expenditure of Research and Development resources. In the majority of cases this problem is solved by the parent invention which is drawn to a generic signaling assay method that is readily adaptable to most target analytes. However, some small analytes are hydrophobic and hard to chemically modify or difficult to work with within the context of the parent invention. The present invention overcomes the problems associated with this sub-set of small analytes while conserving the approach of the parent invention, resulting in greater efficiency of non-invasive immunological screening procedures and reduced Research and Development costs.

Finally, the method of the present invention is highly sensitive, i.e. has a very low detection limit, and yet is more rugged than other methods (such as enzyme-based methods) because the method of the invention has a longer shelf-life and is more forgiving in the hands of a user.

SUMMARY OF THE INVENTION

The invention uses an affinity matrix material for detecting a small analyte target comprising a solid phase sorbent material and a first ligand such as a monoclonal or polyclonal antibody, or a non-antibody ligand specific for the target analyte as well as a conjugated version of the analyte, in which the first ligand is bound to the sorbent material. This aspect of the invention provides a novel and widely useful method of testing for the presence of a small analyte by use of a ligand that binds to both the small analyte and conjugated small analyte, in which the ligand is bound to a solid phase sorbent material. Examples of solid phase sorbent materials are; sepharose and other agarose gel compositions, dextrans, magnetic beads or particles, charged nylon membranes, carbon and silicon granular preparations and the like, including glass beads and plates.

The invention can be summarized as follows. Any small target analyte and any conjugate decorated with multiple target analytes which are capable of competitively binding a first antibody or specific ligand that is linked to a solid support matrix can be employed. A second antibody or specific ligand which recognizes both the analyte and the multiple-analyte-decorated conjugate, and that has a fluorescent label, or any chemical compound that serves as a direct label, including colorimetric and isotopic labels, but specifically excluding all enzymes and indirect signal generators, is used. A sample that is spiked with the multiple-analyte-decorated conjugate is exposed simultaneously, or sequentially, in either order, to the first ligand and the second, tagged ligand. The amount of the label detected indicates the concentration of the endogenous amount of the analyte in the sample in inverse relationship as described below.

A test sample is mixed or may be incubated with a pre-determined amount of the multiple-analyte-decorated conjugate. When the test sample containing the multiple-analyte-decorated conjugate is passed over the immunoaffinity matrix, the first antibodies can bind competitively to two species: free analyte and multiple-analyte-decorated conjugate. The matrix is then exposed to a second ligand, such as a mono- or polyclonal antibody that is tagged or fluorescently labeled. Either within the matrix or upon elution, high label presence is seen in a clean sample. Conversely, only a small amount of the tag or label is detected in the matrix or eluant of a test sample that is highly contaminated with the free analyte.

It is an object of this invention to provide a kit for rapidly and accurately determining the presence or absence of small analytes in a sample quantitatively or non-quantitatively as desired. Each component of the kit(s) may be individually packaged in its own suitable container. The individual containers may also be labeled in a manner which identifies the contents. Moreover, the individually packaged components may be placed in a larger container capable of holding all desired components. Associated with the kit may be instructions that explain how to use the kit. These instructions may be written on or attached to the kit.

The present invention is drawn to a small analyte that is less than 10,000 Da, which is tagged with a non-enzyme label.

The present invention is further drawn to an affinity matrix for the detection of a small analyte comprising:

a solid phase sorbent material; and a first ligand which is specific for both said small analyte and the small analyte which is conjugated or tagged with a non-enzyme label, wherein said first ligand is immobilized on said sorbent material.

The present invention is further drawn to a method for detecting small analytes in a test sample which comprises the steps of:

exposing a sample believed to contain a small analyte in combination with a predetermined amount of said analyte that decorates a non-enzyme conjugate, to a solid phase sorbent material that has immobilized thereon a first ligand that is specific for both said analyte and said multiple-analyte-decorated conjugate;

washing said solid phase sorbent material to remove non-specifically associated sample material;

exposing said solid phase sorbent material to a second ligand which is specific for said analyte and said multiple-analyte-decorated conjugate, and which is tagged or labeled;

washing said solid phase sorbent material to remove non-specifically associated tagged second ligand;

detecting the presence and amount of said tagged second ligand, for example, by subjecting said resin to UV light to induce fluorescence.

In addition, the present invention is further drawn to a method for detecting small analytes in a test sample which comprises the steps of:

exposing a sample believed to contain a small analyte in combination with a predetermined amount of said analyte that decorates a non-enzyme conjugate, to a solid phase sorbent material that has immobilized thereon a first ligand that is specific for both said analyte and said multiple-analyte-decorated conjugate;

washing said solid phase sorbent material to remove non-specifically associated sample material;

exposing said solid phase sorbent material to a second ligand which is specific for said analyte and said analyte-decorated conjugate, and which is tagged or labeled;

washing said solid phase sorbent material to remove non-specifically associated tagged second ligand;

exposing said solid phase sorbent material to a releasing agent, whereby said analyte, analyte-decorated conjugate and tagged second ligand are released from said first ligand;

recovering said analyte, multiple-analyte-decorated conjugate and tagged second ligand in an eluant; and detecting the presence and amount of said tagged second ligand in said eluant, for example, by subjecting said eluant to UV light to induce fluorescence.

In addition, the present invention is further drawn to a kit for detecting small analytes in a test sample, comprising:

a solid phase sorbent conjugated to a first ligand specific for both a small analyte of molecular weight of not more than about 10,000 daltons and said analyte that decorates a conjugate;

a multiple-analyte-decorated conjugate;

a second tagged ligand to be detected that is specific for both said small analyte and said multiple-analyte-decorated conjugate;

instructions for carrying out the detection method.

DETAILED DESCRIPTION OF THE PREFERRED EMBODIMENTS OF THE INVENTION

The present invention is based on the observation that free small analytes as described below, when bound to an antibody or ligand are incapable of binding a second antibody or ligand, unlike larger molecules. In this embodiment of the present invention, a target small analyte and a known quantity of said small analyte decorating a conjugate, compete for binding of an immobilized first antibody or ligand specific to said small analyte and said multiple-analyte-decorated conjugate. After removing unbound material, the immobilized first antibody or ligand with bound small analytes and multiple-analyte-decorated conjugates is exposed to a second, tagged antibody or ligand which is specific to said small analyte and said multiple-analyte-decorated conjugate. Multiple-analyte-decorated conjugates are able to bind the second, tagged antibody or ligand while free small analytes are too small and are, thus, unable to participate in these second binding reactions. The amount of label then detected indicates the concentration of the endogenous amount of the analyte in the sample in an inverse relationship.

The present invention is useful for the detection and isolation of a small analyte generally when it presents two characteristics or, for antibody based assays, three characteristics: first, the target analyte has a molecular weight not greater than about 10,000 daltons; second, in situations where the antibody ligand is used, that the target analyte, either alone or in combination with other compounds, is usually able to induce an immunological response in vivo when introduced into an animal subject; and third that the ligand is capable of recognizing both the free target analyte and a tagged or conjugated analyte.

The first characteristic of a molecular weight not greater than about 10,000 daltons, is easily determinable for any target analyte, including a toxic substance.

The second characteristic, in situations where the antibody ligand is used, the ability of the small analyte to induce an antibody response after introduction into a test animal in vivo, relies on its ability primarily (but not exclusively) to serve as an immunogen.

The third characteristic, the capability of the ligand to recognize the free target analyte as well as the multiple-analyte-decorated conjugate, is easily determinable for any substance and is within the skill of the person of ordinary skill in the art.

The analyte is less than about 10,000 Da, preferably about 6,000 Da, more preferably about 3,000 Da, and most preferably 1,000 Da or less. The analyte is particularly small enough so as to not function in a sandwich assay, i.e. the analyte is too small to be simultaneously bound by two different ligands. The decorated conjugate is comprised of a substance which itself has at least two target anayltes attached thereto, the substance being a protein (such as bovine serum albumin (BSA), ovalbumin (OA), keyhole limpet chemocyanin (KLH) or an antibody), but also including carbohydrates (such as poly- or oligo-saccharides (including glucose or other sugar polymers, pectin, amylose, malto-dextrin or limit-dextrin)), DNA and peptido-nucleic acid (PNA). For example, T-2 toxin is a molecule of less than 10,000 Da. Two or more T-2 toxin molecules can be bound to one BSA molecule to create a "decorated conjugate". In a second form, a "decorated conjugate" could be two T-2 toxin molecules attached to a protein or sugar oligomer serving as a linker and being large enough so that two independent binding sites for T-2 toxin are created, but not so large as to create another binding site independent of the T-2 toxin molecules. The term "ligand" as used herein includes any molecule that specifically recognizes and binds both the free analyte and multiple-analyte-decorated conjugate. A "ligand" can refer to components of a polyclonal anti-serum, monoclonal antibody, or a non-antibody molecule.

The term "non-antibody ligand" as used herein includes non-antibody molecules that can be used to bind the target analyte as well as the multiple-analyte-decorated conjugate of the present invention. Such ligands include, for example, lectins and receptors such as opiate receptors.

The term "label" or "tag" as used herein includes all non-enzymatic compounds that serve as a reporter of the presence of the ligand to which it is bound, and does not prevent the binding of the analyte or the multiple-analyte-decorated conjugate to the tagged ligand. Examples of such labels include those which are radioactive, fluorescent, chemiluminescent, colored or absorbent, or a combination of the foregoing.

Radioactive or isotopic labels include, for example, $^{14}C$ $^{3}H$, $^{35}S$, $^{125}I$ and $^{32}p$. Fluorescent labels include any compound that emits an electromagnetic radiation, preferably visible light, resulting from the absorption of incident radiation and persisting as long as the stimulating radiation is continued. Such compounds include coumarin containing molecules, and further include anthroyl compounds, naphthalene compounds, pyrene compounds, compounds containing benzyl, pyrenyl and phenyl groups, fluorescein compounds, anthracene compounds, compounds containing conjugated pi electron systems, but are not limited to these categories of compounds and include any compound that could be used as a label in this invention.

Examples of the fluorescent coumarin molecules include 7-hydroxycoumarin, 7-aminocoumarin, and further include 6-((7-amino-4-methylcoumarin-3-acetyl)amino)hexanoic acid, succinimidyl ester, 7-amino-3-((((succinimidyl)oxy) carbonyl)methyl)-4-methylcoumarin-6-sulfonic acid, 7-diethylaminocoumarin-3-carboxylic acid, 7-diethylaminocoumarin-3-carboxylic acid succinimidyl ester, 7-diethylamino-3-(4'-isothiocyanatophenyl)-4-methylcoumarin, 7-dimethylaminocoumarin-4-acetic acid, 7-dimethylaminocoumarin-4-acetic acid succinimidyl ester, 7-hydroxycoumarin-3-carboxylic acid, 7-hydroxycoumarin-3-carboxylic acid succinimidyl ester, 7-hydroxy-4-methylcoumarin-3-acetic acid, 7-hydroxy-4-methylcoumarin-3-acetic acid succinimidyl ester, 7-methoxycoumarin-3-carboxylic acid, 7-methoxycoumarin-3-carboxylic acid succinimidyl ester, 7-diethylaminocoumarin-3-carbonyl azide and 7-methoxycoumarin-3-carbonyl azide.

Examples of naphthalene compounds include 6-((5-dimethylaminonaphthalene-l-sulfonyl)amino)hexanoic acid, 2-dimethylaminonaphthalene-5-sulfonyl chloride, dimethylaminonaphthalene-6-sulfonyl chloride, 6-(N-methylanilino)naphthalene-2-sulfonyl chloride, 6-(p-toluidinyl)naphthalene-2-sulfonyl chloride and 5-aziT2aphthalene.

Examples of other fluorescent labels include but not limited to 2,4-dinitrophenyl, acridine, cascade blue, rhodamine, 4-benzoylphenyl, Rosamine, 7-nitrobenz-2-oxa-1,3-diazole, 4,4-difluoro-4-bora-3a,4a-diaza-3-indacene and fluorescamine. Absorbance based labels include molecules which are detectable by the level of absorption of various electromagnetic radiation. Such molecules include, for example, the fluorescent labels indicated above, as well as various dyes which are visibly colored and examinable by the eye, such as indole derivatives which are detectable by calorimetric means.

Chemiluminescent labels in this invention refer to compounds that emit light as a result of a non-enzymatic chemical reaction. An example of a chemiluminescent label applied to T2 would be as follows: Ground-state tagged T2+Chemical compound→Excited derivatized tagged T2+Altered chemical compound→ Ground-state derivatized tagged T2+LIGHT The invention applies generally to all small analytes which meet the above criteria. Specifically included within this class of compounds are pesticides, drugs, toxins, mycotoxins and drug metabolites, and further include trichothecenes, fumonisins, antibiotics, and fragments of microorganisms, such as bacteria, parasites, viruses, yeast and mold.

An entire listing of small analytes is extensive, varied in chemical composition and structure, and expanding in view of the ever increasing list compiled by the U.S. Dept. of Health and Human Services. In view of this, a true and complete listing is neither possible nor desirable and will not be attempted here. Instead a representative example, T-2 toxin, will be the small analyte of choice which is described for use and detection in its conjugated form by the present invention.

T-2 toxin has a molecular weight of about 467 daltons, and is a mycotoxin produced by a fungus belonging to the genus Fusarium, and is found in cereal grain products and products derived from them. It belongs to a class of chemical compounds known as trichothecenes.

Trichothecenes are a family of over 148 structurally related compounds produced by several fungal genera (Fusarium, Cephalosporium, Myrothecium, Stachybotrys, and Trichoderma). Some naturally-occurring trichothecene mycotoxins produced in foods and feeds by Fusarium include deoxynivalenol (DON), T-2, nivalenol (NIV), and diacetoxyscirpenol (DAS).

It is expressly understood, however, that the present invention is not limited to this working example nor to those other substances specifically identified above but rather is suitable instead generally for the entire class of substances which meet the factors described above.

I. Preparing a Non-Antibody Affinity Chromatography

Not all of the specific methodologies available for affinity chromatography will be reviewed here, nor is an exhaustive list of examples for each technique provided. The person of skill in the art will appreciate the technique of finding ligands such as lectins or receptor molecules that are specific for both the free and labeled small analyte-target. To this end, the contents of "Guide to Protein Purification", *Methods In Enzymology*, Vol. 182 (1990), Academic Press, Inc. is incorporated by reference herein in its entirety.

A subset of general affinity chromatography procedures apply to the present invention. Parameters such as temperature, incubation time, pH, ionic strength, and flow rates affect the strength of binding of the target analytes to the specific ligand. Binding a small analyte to a ligand on an affinity chromatography column is achieved by binding the analyte specific ligand that can "recognize" the analyte to the solid phase.

The bead size used as the chromatographic support must be of a size and composition to allow the passage of the analyte between the beads when they are packed in a column. The bed support (frit) at the column outlet must also be of a size and composition that allows passage of the analytes from the column. This allows analytes to pass through without any significant impediment.

An analyte such as a small glycoprotein or glycoprotein fragment may be selected by using the appropriate lectins.

For example, concanavalin A (ConA) will select those proteins containing glucose or mannose in specific linkage in carbohydrate chains, while wheat germ lectin will select those proteins containing N-acetylglucosamine in specific linkage in carbohydrate chains. U.S. Pat. No. 5,250,410, which contents are incorporated herein by reference in its entirety, discloses that lectins are viable means for detecting target molecules. Consequently, the choice of the affinity ligand is dependent on the analyte being purified.

The process of binding analytes to ligands attached to a matrix is very similar to other affinity methods. The procedure is summarized as follows:

1. Prepare a ligand bound resin matrix in a column.
2. Separately mix an analyte containing sample and a predetermined amount of multiple-analyte-decorated conjugate.
3. Apply the mixture to the column.
4. Wash out nonadhering analytes/conjugates.
5. Add elution buffer.
6. Collect the eluant which contains free analytes and multiple-analyte-decorated conjugate. Alternatively,
1. Prepare a ligand bound resin matrix.
2. Mix the ligand bound resin matrix as a suspension or a slurry with an analyte containing sample and a predetermined amount of multiple-analyte-decorated conjugate.
3. Incubate.
4. Pour the mixture slurry into a column.
5. Wash out nonadhering analytes/conjugate.
6. Add elution buffer.
7. Collect the eluant which contains free analytes and multiple-analyte-decorated conjugate.

Covalent Chromatography and Bifunctional Agents

Although binding of most ligands in affinity chromatography is accomplished through the carboxyl or amino groups (especially on proteins), there are other reactive groups that are available under the proper conditions. The use of these groups may make the separation even more specific than if the carboxyl or amino groups were used.

Sulfhydryl-containing matrices can be used to couple proteins containing not only sulfhydryl groups, but also compounds containing $C=O$, $C=C$, $N=N$, as well as heavy metals (e.g., Hg) or alkyl and aryl halides (Locelyn, "Biochemistry of the SH Group. The Occurrence, Chemical Properties, Metabolism and Biological Function of Thiols and Disulphides." Academic Press, New York, 1972, incorporated herein by reference). The matrix for this type of chromatography is made with an active sulfhydryl group that will form a covalent disulfide bond with a ligand protein such as a receptor or an antibody, which is then used to detect the free and tagged analyte of interest. The active group on the matrix is usually a thiopropyl or glutathione moiety. In this type of chromatography a sample or ligand containing thiol groups is bound to the matrix by the formation of a reversible mixed disulfide bond.

The use of covalent chromatography is similar to other affinity chromatography procedures. It is a very powerful method for quickly isolating or detecting thiol-containing analytes.

II. Preparation of T-2 Immunogen

The preferred immunogen is a composition in which T-2 has been conjugated to bovine serum albumin (hereinafter "BSA") after the conversion of T-2 to 3-O-hemisuccinyl-T-2 as previously described (Hunter, K. W. Jr., et al, 1985, *Preparation and Characterization of Monoclonal Antibodies to the Trichothecene Mycotozin* T2, Appl. Environ. Microbiol. 49, pp 168–172 and Hart et al., J. Agric. Food Chem. 36:663–668 (1988), incorporated herein by reference in its entirety). The same procedure was used to conjugate T-2 to gelatin (type IV, SIGMA) for use in screening mouse antisera and hybridoma supernatants by competitive ELISA.

III. Immunization of Mice and Isolation of Polyclonal Antibodies

Female B6SJLF$_1$/J (Jackson Labs), approximately 8 weeks of age, are immunized with T-2-BSA immunogen which has been dissolved in PBS and emulsified with an equal volume of complete Freund's adjuvant. Using two groups of five mice each, immunization is performed by intraperitoneal injection of 50.0 $\mu$g of T-2-BSA (with adjuvant) in a final volume of 0.2 ml PBS. At 4 weeks and 8 weeks post initial injection, each mouse receives an identical quantity of T-2-BSA emulsified with incomplete Freund's adjuvant. Approximately 10 days after the second injection, serum samples are taken from each mouse via the retro-orbital sinus and are assayed for anti-T-2 antibody activity by competitive ELISA immunoassay determination. For those mice showing the presence of specific antibody in their serum, each is given a final immunization of the identical T-2-BSA again in 0.1 ml of PBS injected into the tail vein 3 days prior to sacrifice of the animal.

The competitive ELISA immunoassay also is used to determine the presence of specific antibodies against T-2 in mouse sera (and subsequently to identify specific hybridomas); these assays are modifications of methods previously described in the art (Haugen et al., *Proc. Natl. Acad. Sci. U.S.A.* 78:4124–4127 (1981); Groopman et al., Cancer Res. 42:3120–3124 (1982)). Briefly summarizing the procedure, T-2-gelatin is dissolved in PBS at a concentration of 2.0 $\mu$g/ml and 50 $\mu$l of this fluid mixture is added to each well of a polyvinyl microtiter plate and allowed to incubate for 2–4 hours at ambient temperature. Other wells in the microtiter plate receive 50 $\mu$l of gelatin in PBS at a concentration of 2 $\mu$g/ml and serve as controls.

The fluid in each well is then aspirated and each well is washed 3 times with PBS with 0.05% (vol/vol) TWEEN 20. Subsequently each well receives a PBS solution containing 0.2% gelatin and the plates are allowed to incubate for an additional hour at ambient temperature. This procedure is designed to limit non-specific binding of antibodies. The plates are then washed in PBS with 0.05% TWEEN 20 and 50 $\mu$l aliquots of diluted mouse serum samples (or hybridoma medium) plus appropriate competitor are added to each well. To titer the mouse sera, dilutions in PBS with 0.05% TWEEN 20 are prepared over a range from 1:100–1:51,200 in continuing two-fold dilutions. The microtiter plates are then incubated for 90 minutes at 37° C., after which they are thoroughly washed with PBS+0.05% TWEEN 20. Specific antibodies that become bound to the surface of each well are detected by adding 50 $\mu$l of a 1:1000 dilution of goat anti-mouse IgG+IgM antibody coupled to alkaline phosphatase to each well followed by incubation of 90 minutes at 37° C. The wells in each plate are then rewashed with PBS with TWEEN 20 plus a final wash with tap water. 100 $\mu$l per well of 1.0 mg/ml p-nitrophenyl phosphate solution (Sigma) prepared in 0.1M diethanolamine buffer, pH 9.8 then is added and allowed to react for 30 min. Quantitative measurement of the p-nitrophenol reaction product is performed by measuring the absorbance of the assay well at 405 nanometers using a microtiter plate reader (Dynatech Labs).

The isotypes of the monoclonal antibodies (that is the determination and identification of different antibody heavy chain class) are determined in a non-competitive ELISA methodology using a commercially purchased kit for mouse immunoglobulin subtype identification (Boeringer-Mannheim Company).

IV. Preparation of Hybridomas and Isolation of Monoclonal Antibody Producing Cells The female B6SJLF$_1$/J mice previously immunized with T-2-BSA in complete Freund's adjuvant are tested for production of significant anti-T2 serum titers using the competitive ELISA methodology as described above. Those mice showing high titers are sacrificed and hybridomas prepared following the procedures previously described in Marshak-Rothstein et al., *J. Immun.*, 122:2491–2497 (1979). The myeloma cell line used for cell fusion are P3-X63/Ag8.653 cells which were maintained in Dulbecco's Modified Eagles medium (hereinafter "DME" medium) supplemented with 20% (volume/volume) fetal calf serum, 2 mM L-Glutamine, 10 units/ml penicillin, 100 $\mu$g/ml streptomycin, and non-essential amino acids (Gibco). The mice are sacrificed and spleen cell suspensions prepared using Hanks' balance salt solution buffered with 0.01M phosphate, pH 7.2 (hereinafter "HPBS").

The spleen cells from these mice are fused with P3-X63/Ag8.653 myeloma cells using a modification of the Gefter et al. procedure (*Somatic Cell Genet.* 3:321 (1977)). Unless stated otherwise, all centrifugations are performed at 700 times gravity for 5 minutes at room temperature. Preferably, $5\times10^6$ P3-X63/Ag8.653 myeloma cells and $2.5\times10^7$ immune spleen cells are combined in a round bottom plastic tube, centrifuged, resuspended in 10 ml of serum free DME medium and centrifuged again. The supernatant is carefully discarded and the centrifuge tube tapped sharply to disperse the residual cell pellet. The cells are then exposed to 0.5 ml of a 30% (volume/volume) solution of polyethylene glycol 1000 (Baker Chemical Company) in serum free DME for 6 minutes. During this 6 minute period, the cell suspension is gently centrifuged (150×gravity for 3 minutes). 4.0 ml of serum free DME is then added to the cell pellet and the cells again resuspended by tapping the tube. The contents of the tube are transferred to 100×17 mm Petri dishes and cultured in DME medium containing 20% fetal calf serum for 1 day. The cells are then centrifuged again and resuspended in growth medium containing hypoxanthine, aminopterin and thymidine (hereinafter "HAT medium"). 0.1 ml aliquots of the cells are then distributed into the wells of flat bottom microtiter dishes, each aliquot containing approximately 105 P3-X63/Ag8.653 cells. After one week's incubation, 0.05 ml of growth medium containing only hypoxanthine and thymidine (hereinafter "HT medium") is added to each well. Cultures are screened for specific anti-T-2 antibody activity two weeks post fusion using the competitive ELISA immunoassay technique described earlier.

Hybridomas secreting monoclonal antibodies of high affinity specific for T-2 are grown as ascites tumor cells in Scid mice which has been previously injected with 0.5 ml pristane (Aldrich). The hybridomas growing within the mice produce large quantities of specific monoclonal antibodies which are harvested and collected as ascites fluid from each mouse before it dies. The collected fluid from these animals is pooled and either used directly in the immunoassays or further purified by saturated ammonium sulfate precipitation and dialyzed against PBS. Gross pathological examination shows that all mice die as a result of widespread tumor invasion—that is growth of the injected hybridoma cells.

V. Affinity Matrix Comprising Immobilized Anti-T-2 Monoclonal Antibody

An affinity matrix material is prepared using this purified monoclonal antibody following the procedures described by Pharmacia Fine Chemicals. Sufficient (32.0 mg) monoclonal antibody is dissolved in coupling buffer comprising 0.1M $NaHCO_3$, pH 8.3 and 0.5M NaCl to form a 2.0 mg/ml solution. This antibody solution is added to 2.5 g of cyanogen bromide activated Sepharose-4B (Sigma) which has been incubated previously in 8.0 ml of 0.001M HCl overnight. After the Sepharose and antibody solution are allowed to react for 1 hour, the unbound sites of the antibody bound gel are blocked by incubating the solid phase sorbant material with 0.1 M Tris, pH 8.3 for 1 hour. The combination of the monoclonal antibody immobilized onto the solid phase sorbant material form an affinity matrix which then was used in volumes of from 0.3–0.5 ml.

Although the preferred solid phase sorbant material is the activated Sepharose 4B gel, it is recognized that many other materials may be substituted as the solid phase material. These include other agarose gel compositions, dextrans, membranes, carbon and silicon granular preparations and the like, including glass plates. Similarly, methods for immobilizing the monoclonal or polyclonal antibody or an analyte specific non-antibody ligand onto each of these different chemical compositions are known and described in the art. For this reason, the preparation of a solid phase sorbant material which is then coupled to any specific ligand as described herein in any form, concentration, or configuration is deemed to be within the scope of the present invention.

VI. Methodology for Tagging a T-2 Antibody

Not all of the specific methodologies available will be reviewed here, nor is an exhaustive list of examples for each technique provided. In brief, antibodies can be labeled directly or indirectly with a variety of signaling agents, for example, radioisotopes and fluorochromes. The preferred tags are fluorochromes. Indirect antibody-fluorochrome labeling entails the use of suitable secondary reagents previously conjugated to fluorochromes; these reagents may be commercially available. Four fluorochromes are commonly used: fluorescein, rhodamine, Texas red and phycoerytherin.

Fluorescein (FITC) and rhodamine (TRITC) isothiocyante derivatives are available for coupling reactions preformed according to Goding (Goding, J W (1976) J. Immunol. Methods 13: 215–226). In brief, this method uses a 1 mg/ml solution of the dye derivative dissolved in dimethyl sulfoxide. An antibody solution having a concentration of at least 2 mg/ml protein in 0.1 M sodium carbonate (pH 9.0) is gently stirred and the dye solution added at a ratio of 50 $\mu$l for each 1 ml of antibody solution. After an incubation of 8 hours at 4° C. in the dark, $NH_4Cl$ is added to 50 mM and incubation continued for another 2 hrs, whereupon xylene cylanol is added to 0.1% and glycerol to 5%. Unbound dye is then separated from the conjugate by passing the reaction over a phosphate buffer (PBS) equilibrated gel filtration column composed of fine sized beads (~50 $\mu$m in diameter) with an exclusion limit of 20,000–50,000. The conjugated antibody elutes first and generally is visible under room light. This conjugate can be stored at 4° C. in a lightproof container with or without the addition of sodium azide to 0.02%. Low concentrations of conjugate (for example less than 1 mg/ml) remain more stable with the addition of BSA to a final concentration of 1%. To estimate the ratio of fluorescein to protein, the absorbance at 495 nm and 280 nm is determined. The optimum range of 0.3–1.0. Rhodamine estimations measure absorbance at 575 and 280 nm, and have an optimum range of 0.3–0.7. Reaction products with ratios lower than the optimum are best discarded and the reaction repeated using lower levels of antibody and higher levels of dye. In addition to repeating reactions with higher antibody and lower dye levels, reaction products with ratios higher than the optimum can be further purified by separation on a 10 mM potassium phosphate (pH 8.0) equilibrated DEAE column. Elution with increasing salt concentrations and measurement of the absorbance ratios of each fraction allow selection and pooling of appropriate fractions.

Alternatively, fluorescein can be coupled to antibodies or other proteins using the methods of Blakeslee and Baines (1976; J Immunol. Methods 13: 305–320) and Blakeslee (1977; J. Immunol. Methods 17: 361–354). Here an antibody solution of at least 2 mg/ml in 0.2M sodium carbonate (pH 9.0) is mixed gently while a 2.5 mg/ml solution of dichlorotriazinlyaminoflurescein (DTAF) in 1.0 M sodium carbonate (pH 9.0) is added at 25 $\mu$g of DTAF per milligram of antibody. After mixing for 10 minutes at room temperature, $NH_4Cl$ is added to 50 mM and the reaction incubated for 2 hours at 4° C. Xylene cylanol is added to 0.1% and glycerol to 5% before the unbound dye is separated from the DTAF by gel filtration in the same manner as described above. Likewise, estimation of the success of the coupling reaction is conducted as for FITC coupling.

VII. Methodology for Conjugating T-2

The method for conjugating T-2 is essentially the same as that for preparing a T-2 immunogen. However, a variety of substances can be used as the conjugate for T-2. Suitable proteins are bovine serum albumin (BSA), ovalbumin (OA), keyhole limpet chemocyanin (KHL) or an antibody. Other suitable substances are carbohydrates, such as poly-or oligo-saccharides (including glucose or other sugar polymers, pectin, amylose, malto-dextrin or limit-dextrin), DNA or peptido-nucleic acids (PNA).

Not all of the specific methodologies for performing conjugation reactions are listed or reviewed. One skilled in the art will appreciate the techniques of performing a conjugation reaction of a small analyte to an appropriate substance. Examples of different methods used by those skilled in the art to produce conjugates can be found in Hart et al. (J. Agric. Food Chem. 36:663–668 (1988); incorporated herein by reference in its entirety), Wisdom (Peptide Antigens: A practical approach, IRL Press, Oxford, UK (1994); incorporated herein by reference in its entirety) and Van Regenmortel (Synthetic polypeptides as antigens, Elsevier, Amsterdam (1988); incorporated herein by reference in its entirety).

VIII. Methodology for Detecting T-2 in a Fluid Sample

The method for detecting T-2 in a test sample may be carried out using any ligand that is specific for T-2 and a multiple- T-2-decorated conjugate. However, as an example, without limiting the invention in any way, an antibody ligand may be used to detect T-2 by combining aspects of the techniques of ELISA and affinity chromatography while being neither alone. The method of the present invention lacks the enzyme driven signaling system of ELISA. In addition, the method of the present invention does not solely isolate target analyte at high efficiency, as does affinity chromatography.

One embodiment of the method of the present invention comprises the following steps: 1)Preparing an affinity matrix comprising first antibodies which are specific for both the free T2 and conjugated T-2, which have been immobilized onto a solid phase sorbent material; 2) adding a known amount of multiple-analyte-decorated conjugate to the sample to be tested; 3) combining the test sample with the affinity matrix such that a portion of the free T-2 and conjugated T-2 which is present in the test sample binds to and is retained by the antibodies of the affinity matrix; 4) washing the matrix; 5) exposing the affinity matrix to a second tagged antibody which is specific for both the free T-2 and conjugated T-2; 6) washing the matrix; and 7) identifying the presence and amount of the tagged second antibody bound to the affinity matrix. All anti-T-2 antibodies used in this affinity matrix have an affinity constant of at least about 1×105 liters per mole.

A second embodiment of the method of the present invention comprises said steps 1–6 followed by adding a releasing agent such as acetonitrile, methanol or ethanol to the affinity matrix to release all bound free and conjugated T-2 from the antibodies on the matrix; and identifying the presence and amount of the tagged second antibody in the eluant collected from the affinity matrix. All anti-T-2 antibodies used in this affinity matrix have an affinity constant of at least about $1\times10^5$ liters per mole.

T-2 antibody columns are bound at about 12 mg/ml, preferably about 10 mg/ml, more preferably about 8 mg/ml, even more preferably about 6 mg/ml, even more preferably about 4 mg/ml, and most preferably about 2 mg/ml which column is about 1 ml in size, preferably 500 μl, more preferably 300 μl, even more preferably 200 μl, and most preferably 100 μl in size.

The invention is more clearly understood from the outline of the detection step using T-2, an antibody as the exemplified ligand and a fluorophore as the exemplified tag as indicated below. A general outline for the overall process in flow-through and incubation formats is set forth below.

Incubation Format

The incubation format is easy to carry out and provides consistency in the results that are obtained.

1. Obtain sample and grind
2. Add 50g ground sample, 10 g PEG, and 5g salt to a blender jar
3. Blend the sample for 1 minute on high speed
4. Filter through a paper filter paper and a glass microfiber filter paper with a pore size of 1.0 μm (This step separates out particulates.)
5. Add 8 ml of extract to a syringe barrel
6. Add 4.0 μg of multiple-T-2-decorated conjugate to the syringe barrel with bottom cap on
7. Add 500 μl of the ligand bound (or in this example, antibody bound) resin slurry (3:2 with PBS) to the syringe barrel (300 μl column equivalent)
8. Cap the syringe barrel and incubate by rotating for about 5 minutes
9. Empty contents of the syringe barrel into a column(with a 1 ml column housing attached and containing a bottom frit so the resin is captured)
10. Pass quickly to pack the resin
11. Wash once with 10 ml 1×PBS (This step removes self-fluorescing molecules.)
12. Wash once with 10 ml water
13. Add fluorescent ligand, e.g. fluorescein labeled antibody 14. Wash with 10 ml water 15. Elute with 1.5 ml ethanol 16. Read in a calibrated fluorometer Non-Incubation or Flow-Through Format The flow-through format does not require incubation. Therefore, the test is more rapid, but will tend to be less accurate and less precise.

1. Obtain sample and grind
2. Add 50 g ground sample, 10 g PEG, and 5 g salt to a blender jar
3. Blend the sample for 1 minute on high speed
4. Filter through a paper filter and a 1.0 μm glass microfiber filter
5. Add 6 ml of extract to syringe barrel (with a 200 μL antibody column attached)
6. Add 2.0 μg multiple-T-2-decorated conjugate to the syringe barrel and mix well
7. Pass extract at 1–2 drop/sec
8. Wash once with 10 ml 1×PBS
9. Add fluorescent ligand, e.g. fluorescein labeled antibody
10. Wash once with 10 ml water
11. Elute with 2×0.75 ml methanol (optionally, 1×elution with methanol)
12. Read in a calibrated fluorometer From the above, it can be seen that the present invention provides a means for easily and accurately detecting levels of various small analytes in a sample. An important aspect of the invention is the combined use of a multiple-analyte-decorated conjugate, an affinity matrix or column to which is bound the specific first ligand that binds both the free analyte and the multiple-analyte-decorated conjugate, and a second tagged ligand that binds both the free analyte and the multiple-analyte-decorated conjugate. The use of such an affinity matrix provides a means for quick and efficient detection of the tagged second ligand in the sample.

The ligand affinity matrix of the invention permits an improved one-step detection method of a sample containing any small analyte, as well as quantitatively assaying for the presence of the analyte in a test sample. The invention is applicable to detecting a variety of analytes in a variety of samples including industrial waste and food, as well as small analytes such as hallucinogens and narcotics in bodily fluids. Such testing, according to the invention, can be accomplished with the use of any label and a ligand specific for the free analyte and the multiple-analyte-decorated conjugate that is bound to a solid phase sorbent.

EXAMPLES

What is claimed is:

1. A method for detecting a small analyte in a test sample, said method comprising:

combining a sample believed to contain a small analyte with a known amount of a multiple-analyte conjugated substance, wherein said analyte is small enough so that it cannot be simultaneously bound by two different ligands;

exposing said sample to a solid phase sorbent material that has immobilized thereon a first ligand that is specific for both said small analyte and said multiple-analyte conjugated substance;

exposing said solid phase sorbent material to a second ligand that is tagged and that is specific for both said analyte and said multiple-analyte conjugated substance;

detecting the presence and amount of said tagged ligand, which amount indicates the concentration of the analyte in the sample in an inverse relationship.

2. A method for detecting a small analyte in a test sample, said method comprising:

combining a sample believed to contain a small analyte with a known amount of a substance to which multiple said analytes have been conjugated, wherein said analyte is small enough so that it cannot be simultaneously bound by two different ligands;

exposing said sample to a solid phase sorbent material that has immobilized thereon a first ligand that is specific for both said analyte and said multiple-analyte conjugated substance;

exposing said sample sorbent material to a second ligand that is tagged and that is specific for both said analyte and said multiple-analyte conjugated substance;

separating any free, unrelated material from said solid phase sorbent material;

exposing said solid phase sorbent material to a releasing agent to recover said analyte, said multiple-analyte conjugated substance and said tagged ligand in an eluant; and detecting the presence and amount of said tagged ligand which amount indicates the concentration of the analyte in the sample in an inverse relationship.

3. The method according to claim 2, wherein said releasing agent comprises a not less than 50% solution of an aprotic solvent or a 50–100% solution of a lipophilic solvent, or an organic solvent, a carbohydrate solution or a buffer of high or low pH or salt content.

4. The method according to claim 3, wherein said solvent comprises 100% acetonitrile, 100% methanol or 100% ethanol.

5. The method according to claim 2, wherein said analyte is a member selected from the group consisting of a pesticide, a drug, a toxin, a mycotoxin, a drug metabolite, a tricothecene, a fumonisin, an antibiotic, a fragment of a microorganism, and a fragment of a mammalian cell.

6. The method according to claim 5, wherein said analyte is a toxin or a conjugate or derivative thereof.

7. The method according to claim 6, wherein said toxin is T-2 toxin.

8. The method according to claim 6, wherein said substance is a member selected from the group consisting of a non-enzymatic protein, a carbohydrate, a deoxyribonucleic acid (DNA), a peptide nucleic acid (PNA), a lipid, and a lipid derivative.

9. The method according to claim 6, wherein said tag is a fluorescent label.

10. The method according to claim 9, wherein said fluorescent label is an anthroyl group.

11. The method according to claim 9, wherein said label is a coumarin.

12. A method for detecting T-2 toxin in a test sample, said method comprising:

combining a sample believe to contain T-2 toxin with a known amount of a multiple-T-2 toxin-bovine serum albumin (BSA) conjugate comprised of BSA to which is conjugated at least two T-2 toxin molecules, wherein said T-2 toxin is small enough so that it cannot be simultaneously bound by two different antibodies;

exposing said sample to a solid phase sorbent material that has immobilized thereon a first antibody that is specific for both said T-2 toxin and said multiple-T-2 toxin-BSA conjugate;

exposing said solid phase sorbent material to a second antibody that is tagged and that is specific for both T-2 toxin and said multiple-T-2 toxin-BSA conjugate;

separating any free, unreacted material from said solid phase sorbent material;

exposing said solid phase sorbent material to a releasing agent to recover said T-2 toxin, said muletiple-T-2 toxin conjugated BSA and said tagged antibody in an eluant; and detecting the presence and amount of said tagged antibody, which amount indicates the concentration of T-2 toxin in the sample in an inverse relationship.

13. A kit for detecting analytes in a test sample, comprising:

a solid phase sorbent material conjugated to a first ligand specific for both a small analyte of molecular weight of not more than about 10,000 daltons and a multiple-analyte conjugated substance, wherein said analyte is small enough so that it cannot be simultaneously bound by two different ligands, and said analyte is selected from the group consisting of a mycotoxin, a fumonisin, and a T-2 toxin;

a substance conjugated to at least two of said small analyte;

a tagged second ligand to be detected that is specific for both a small analyte of molecular weight of not more than about 10,000 daltons and said multiple-analyte conjugated substance;

and instructions for carrying out a detection method.

14. The kit according to claim 13, wherein said analyte is a mycotoxin.

15. The kit according to claim 13, wherein said analyte is fumonisin.

16. The kit according to claim 13, wherein said analyte is T-2 toxin.

17. The kit according to claim 13, wherein said conjugated substance is a member selected from the group consisting of non-enzymatic proteins, carbohydrates, a deoxyribonucleic acid (DNA), a peptide nucleic acid (PNA), a lipid, and a lipid derivative.

18. The kit according to claim 13, wherein said conjugated substance is bovine serum albumin (BSA).

19. The kit according to claim 13, wherein said first and second ligands are antibodies.

20. The kit according to claim 13, wherein said tag is a fluorescent label.

* * * * *